United States Patent
Smith et al.

(10) Patent No.: US 9,290,481 B2
(45) Date of Patent: Mar. 22, 2016

(54) MONOCYCLIC HETEROARYL CYCLOALKYLDIAMINE DERIVATIVES

(71) Applicants: Alexander Baxter Smith, Niffer (FR); Gebhard Thoma, Lorrach (DE); Maurice Van Eis, St. Louis (FR)

(72) Inventors: Alexander Baxter Smith, Niffer (FR); Gebhard Thoma, Lorrach (DE); Maurice Van Eis, St. Louis (FR)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/400,545

(22) PCT Filed: May 15, 2013

(86) PCT No.: PCT/IB2013/053970
§ 371 (c)(1),
(2) Date: Nov. 11, 2014

(87) PCT Pub. No.: WO2013/171690
PCT Pub. Date: Nov. 21, 2013

(65) Prior Publication Data
US 2015/0152087 A1    Jun. 4, 2015

Related U.S. Application Data

(60) Provisional application No. 61/647,675, filed on May 16, 2012.

(51) Int. Cl.
| C07D 403/12 | (2006.01) |
|---|---|
| A61K 31/53 | (2006.01) |
| A61K 31/497 | (2006.01) |
| A61K 45/06 | (2006.01) |
| A61P 19/02 | (2006.01) |

(52) U.S. Cl.
CPC ............ *C07D 403/12* (2013.01); *A61K 31/497* (2013.01); *A61K 31/53* (2013.01); *A61K 45/06* (2013.01)

(58) Field of Classification Search
CPC .. C07D 430/12; C07D 403/182; A61K 31/53; A61K 45/06
USPC .......................................... 544/182; 514/242
See application file for complete search history.

(56) References Cited

U.S. PATENT DOCUMENTS

| 2005/0107386 A1 | 5/2005 | Narla et al. |
| 2013/0116430 A1 | 5/2013 | Fujiwara et al. |
| 2013/0131040 A1 | 5/2013 | Song et al. |

FOREIGN PATENT DOCUMENTS

| EP | 1054004 A1 | 11/2000 |
| JP | 8242859 A2 | 9/1996 |
| JP | 2004203748 A2 | 7/2004 |
| WO | 9425565 A1 | 11/1994 |
| WO | 9502686 A1 | 1/1995 |
| WO | 0075113 A1 | 12/2000 |
| WO | 0140800 A3 | 6/2001 |
| WO | 2005027848 A2 | 3/2005 |
| WO | 2005/102215 A1 | 11/2005 |
| WO | 2006068770 A1 | 6/2006 |
| WO | 2007/124221 A1 | 11/2007 |
| WO | 2008014420 A2 | 1/2008 |
| WO | 2009020990 A1 | 2/2009 |
| WO | 2009136995 A2 | 11/2009 |
| WO | 2011045352 A2 | 4/2011 |
| WO | 2011100341 A1 | 8/2011 |
| WO | 2012/021964 A1 | 2/2012 |
| WO | 2012/044936 A1 | 4/2012 |
| WO | 2012045010 A1 | 4/2012 |
| WO | 2012/061418 A2 | 5/2012 |
| WO | 2012/071042 A1 | 5/2012 |
| WO | 2013047813 A1 | 4/2013 |

OTHER PUBLICATIONS

Geahlen R.L.,Trends in Pharmacological Sciences Aug. 2014, vol. 35, No. 8, 414-422.*
Scott et al., Drugs (2014) 74:415-422.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*

(Continued)

*Primary Examiner* — Venkataraman Balasubramanian
(74) *Attorney, Agent, or Firm* — John B. Alexander

(57) ABSTRACT

The present invention relates to monocyclic heteroaryl cycloalkyldiamine derivatives of formula (I), to processes for their production, to their use as pharmaceuticals and to pharmaceutical compositions comprising them.

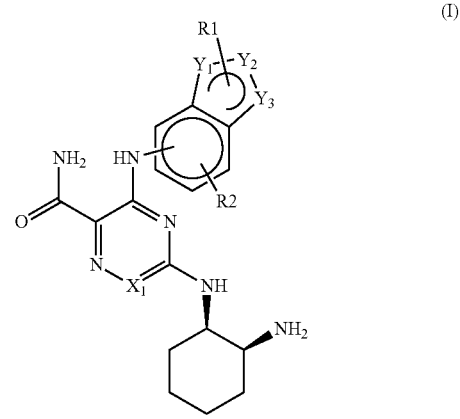

6 Claims, No Drawings

(56) References Cited

OTHER PUBLICATIONS

Golub et al., Science, 286, 531-537, 1999.*

Muller, B. et al, "Molecular cloning of the human homologue to the pig protein-tyrosine kinase syk," Immunogenetics 39:259-362 (1994).

Oliver J.M. et al, "Inhibition of Mast Cell FceR1-mediated Signaling and Effector Function by the Syk-selective Inhibitor, Piceatannol," J Biol Chem 269(47):29697-29703 (Nov. 25, 1994).

Wong, B. et al, "Targeting Syk as a treatment for allergic and autoimmune disorders," Expert Opinion Investigational Drugs 13(7):743-762 (2004).

* cited by examiner

MONOCYCLIC HETEROARYL CYCLOALKYLDIAMINE DERIVATIVES

This application is a U.S. National Phase filing of International Application No. PCT/IB2013/053970 filed 15 May 2013, which claims priority to U.S. Application No. 61/647,675 filed 16 May 2012, the contents of which are incorporated herein by reference in their entirety.

The present invention relates to monocyclic heteroaryl cycloalkyldiamine derivatives, to processes for their production, to their use as pharmaceuticals and to pharmaceutical compositions comprising them.

Spleen tyrosine kinase (SYK), along with ZAP70, has been described to be a member of the SYK-family of tyrosine kinases.

It has been further described that SYK may play a central role in the transmission of activating signals within B-cells. Consequently the inhibition of SYK appears to be beneficial in the treatment of autoimmune diseases.

The role of SYK in epithelial malignancies is at present controversial. Several authors have suggested that abnormal Syk function facilitates transformation in nasopharyngeal carcinoma and head and neck cancer while other authors have suggested a tumor suppressor role in breast and gastric cancer.

The compounds of the present invention typically show potent SYK-inhbition, and are therefore potentially useful in the treatment of a wide range of disorders, for example in the treatment of disease and/or disorders associated with the autoimmune system.

The invention therefore provides a compound of the formula (I) or a pharmaceutically acceptable salt thereof, (I)

wherein

X1 is CH or N;

Y1, Y2 and Y3 are depending on the position of the double bond independently of each other CH, NH or N, and the bent bond indicates aromaticity of the ring system;

R1 is H, alkyl, CN, or Hal; and

R2 is H, alkyl, or Hal.

As used herein the structural part (L) in a compound of formula (I) is a fully aromatic bicyclic system containing at least 1 nitrogen atom represented by anyone of the members Y1, Y2 and Y3.

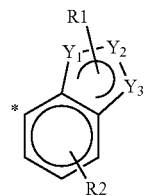

Representative examples for (L) are a 1-indole, 2-indole, 1-indazole, 2-indazole, benzimidazole, benztriazole and tautomers thereof.

In another embodiment structural part (L) in a compound of formula (I) is attached to the remaining part of the molecule at the position indicated by an asterix (*).

In another embodiment the invention provides a compound of formula (I) or a pharmaceutically acceptable salt thereof, wherein X1 is N;

Y1 is NH, Y2 is N and Y3 is CH; or

Y1 is CH, Y2 is N and Y3 is NH;

R1 is H, $C_{1-4}$alkyl, CN, or Hal; and

R2 is H, $C_{1-4}$alkyl or Hal.

In another embodiment the invention provides a compound of formula (I) or a pharmaceutically acceptable salt thereof, wherein X1 is N;

Y1 is NH; Y2 and Y3 are CH;

R1 is H, $C_{1-4}$alkyl, CN, or Hal; and

R2 is H, $C_{1-4}$alkyl or Hal.

In another embodiment the invention provides a compound of formula (II) or a pharmaceutically acceptable salt thereof, wherein (II)

X1 is CH or N;

R1 is H, $C_{1-4}$alkyl, CN, or Hal; and

R2 is H, $C_{1-4}$alkyl or Hal.

In another embodiment the invention provides a compound of formula (II) or a pharmaceutically acceptable salt thereof, wherein X1 is CH;

R1 is H, $C_{1-4}$alkyl, CN, or Hal; and

R2 is H, $C_{1-4}$alkyl or Hal.

In another embodiment the invention provides a compound of formula (II) or a pharmaceutically acceptable salt thereof, wherein X1 is CH;

R1 is H or methyl; and

R2 is H or fluoro.

In another embodiment the invention provides a compound of formula (II) or a pharmaceutically acceptable salt thereof, wherein X1 is N;

R1 is H, $C_{1-4}$alkyl, CN, or Hal; and

R2 is H, $C_{1-4}$alkyl or Hal.

In another embodiment the invention provides a compound of formula (II) or a pharmaceutically acceptable salt thereof, wherein X1 is N;

R1 is H or methyl; and

R2 is H or fluoro.

In another embodiment the invention provides a compound of formula (II) or a pharmaceutically acceptable salt thereof, wherein X1 is N, and wherein R1 and R2 are both hydrogen.

In another embodiment the invention provides a compound of formula (III) or a pharmaceutically acceptable salt thereof, wherein R is H or $C_{1-4}$alkyl;

R1 is H, $C_{1-4}$alkyl, CN, or Hal; and

R2 is H, $C_{1-4}$alkyl or Hal.

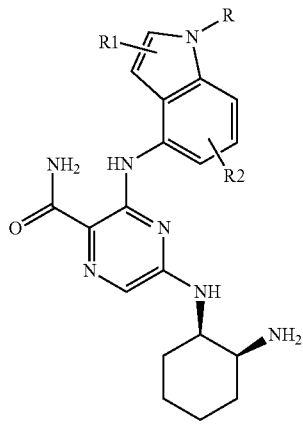

(III)

In another embodiment the invention provides a compound of formula (III) or a pharmaceutically acceptable salt thereof, wherein R is methyl;

R1 is H or methyl; and

R2 is H, methyl or fluoro.

In another embodiment the invention provides a compound of formula (IV) or a pharmaceutically acceptable salt thereof, wherein R1 is H, $C_{1-4}$alkyl, CN, or Hal; and R2 is H, $C_{1-4}$alkyl or Hal.

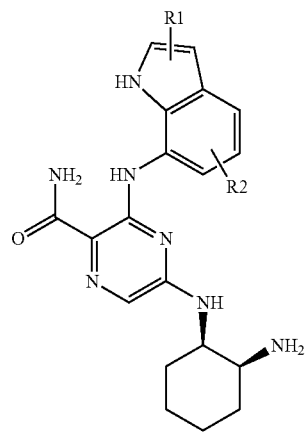

(IV)

In another embodiment the invention provides a compound of formula (IV) or a pharmaceutically acceptable salt thereof, wherein R1 is H or methyl; and R2 is H, methyl or fluoro.

In another embodiment the invention provides a compound of formula (IV) or a pharmaceutically acceptable salt thereof, wherein R1 is H or methyl; and R2 is H.

In another embodiment the invention provides a compound of formula (V) or a pharmaceutically acceptable salt thereof,

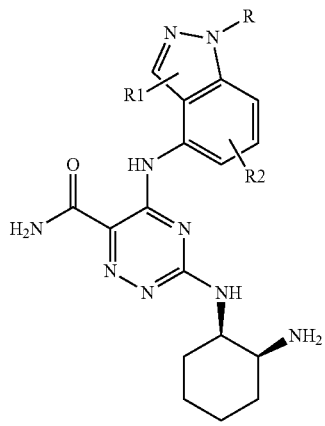

(V)

wherein

R is H or $C_{1-4}$alkyl;

R1 is H, $C_{1-4}$alkyl, CN, or Hal; and

R2 is H, $C_{1-4}$alkyl or Hal.

In another embodiment the invention provides a compound of formula (V) or a pharmaceutically acceptable salt thereof, wherein R is H or methyl, in particular methyl; and R1 and R2 are H.

In another embodiment the invention provides a compound of formula (VI) or a pharmaceutically acceptable salt thereof,

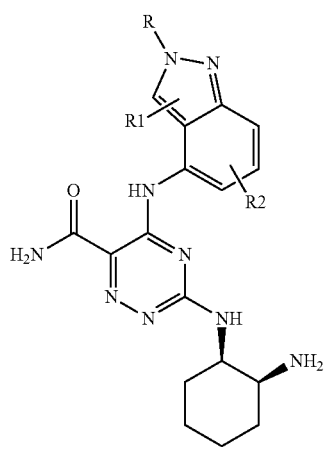

(VI)

wherein
R is H or $C_{1-4}$alkyl;
R1 is H, $C_{1-4}$alkyl, CN, or Hal; and
R2 is H, $C_{1-4}$alkyl or Hal.

In another embodiment the invention provides a compound of formula (VI) or a pharmaceutically acceptable salt thereof, wherein
R is hydrogen or $C_{1-4}$alkyl, in particular methyl; and
R1 and R2 are both hydrogen.

In another embodiment the invention provides a compound of the invention, e.g. a compound of formula (I)-(VI) or a pharmaceutically acceptable salt thereof, wherein said compound is selected from:

3-((1R,2S)-2-Amino-cyclohexylamino)-5-(1H-indol-7-ylamino)-[1,2,4]triazine-6-carboxylic acid amide;
3-((1R,2S)-2-Amino-cyclohexylamino)-5-(5-fluoro-3-methyl-1H-indol-7-ylamino)-[1,2,4]triazine-6-carboxylic acid amide;
3-((1R,2S)-2-Amino-cyclohexylamino)-5-(3-methyl-1H-indol-7-ylamino)-[1,2,4]triazine-6-carboxylic acid amide;
3-((1R,2S)-2-Amino-cyclohexylamino)-5-(1H-indol-4-ylamino)-[1,2,4]triazine-6-carboxylic acid amide;
3-((1R,2S)-2-Amino-cyclohexylamino)-5-(1-methyl-1H-indazol-4-ylamino)-[1,2,4]triazine-6-carboxylic acid amide;
3-((1R,2S)-2-Amino-cyclohexylamino)-5-(2-methyl-2H-indazol-4-ylamino)-[1,2,4]triazine-6-carboxylic acid amide;
3-((1R,2S)-2-Amino-cyclohexylamino)-5-(3-chloro-1H-indol-7-ylamino)-[1,2,4]triazine-6-carboxylic acid amide;
3-((1R,2S)-2-Amino-cyclohexylamino)-5-(3-cyano-1H-indol-7-ylamino)-[1,2,4]triazine-6-carboxylic acid amide;
3-((1R,2S)-2-Amino-cyclohexylamino)-5-(1H-indazol-4-ylamino)-[1,2,4]triazine-6-carboxylic acid amide;
3-((1R,2S)-2-Amino-cyclohexylamino)-5-(5-fluoro-1H-indol-7-ylamino)-[1,2,4]triazine-6-carboxylic acid amide;
5-((1R,2S)-2-Amino-cyclohexylamino)-3-(1-methyl-1H-indol-4-ylamino)-pyrazine-2-carboxylic acid amide;
5-((1R,2S)-2-Amino-cyclohexylamino)-3-(1H-indol-7-ylamino)-pyrazine-2-carboxylic acid amide; and
5-((1R,2S)-2-Amino-cyclohexylamino)-3-(3-methyl-1H-indol-7-ylamino)-pyrazine-2-carboxylic acid amide.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "halogen" or "halo" refers to fluoro, chloro, bromo, and iodo.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

In another embodiment the invention relates to any one of the individual compounds of the invention disclosed and described in the experimental section of this application, each forming a pharmaceutically acceptable salt with each individual acid listed above.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

In another embodiment the invention relates to any one of the individual compounds of the invention disclosed and described in the experimental section of this application, each forming a pharmaceutically acceptable salt with each individual acid listed above.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the the invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, e.g. compounds of formula (I) that contain groups capable of acting as donors and/or acceptors for hydrogen bonds may be capable of forming co-crystals with suitable co-crystal formers. These co-crystals may be prepared from compounds of the invention by known co-crystal forming procedures. Such procedures include grinding, heating, co-subliming, co-melting, or contacting in solution compounds of the invention with the co-crystal former under crystallization conditions and isolating co-crystals thereby formed. Suitable co-crystal formers include those described in WO 2004/078163. Hence the invention further provides co-crystals comprising a compound of the invention.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by SYK, or (ii) associated with SYK activity, or (iii) characterized by activity (normal or abnormal) of SYK; or (2) reducing or inhibiting the activity of SYK; or (3) reducing or inhibiting the expression of SYK. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of SYK; or at least partially reducing or inhibiting the expression of SYK.

The term "subject" as used herein may refer to an animal. The animal may be a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc. Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Methods of Synthesizing

Agents of the invention, for example compounds in accordance to the definition of formula (I), (II), (Ill), (IV), (V) or (VI) may be prepared by a reaction sequence provided infra or explicitly shown in the reaction schemes of the experimental part (see hereinbelow).

In another embodiment the invention relates to a process of manufacturing a compound of formula (I) or a pharmaceutically acceptable salt thereof,

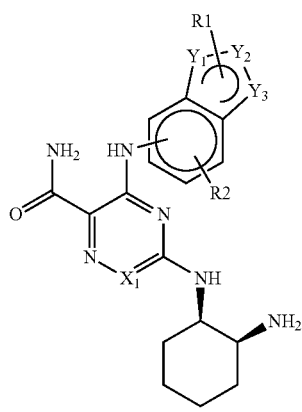

(I)

wherein

X1 is N;

Y1, Y2 and Y3 are depending on the position of the double bond CH, NH or N, and the bent bond indicates aromaticity of the ring system;

R1 is H, alkyl, CN, or Hal; and

R2 is H, alkyl, or Hal;

wherein in accordance to the scheme shown below, a carboxylic acid derivative (1), wherein Alk is alkyl and typically is ethyl, is reacted with an amino-derivative (2) in the presence or absence of a solvent, e.g. in the presence of an aprotic solvent such as NMP, to yield intermediate (3), wherein if a free amino group is present said amino group is then protected in an optional protecting step, e.g. by reacting intermediate (3) e.g. with an agent yielding a protective group such as $BOC_2O$ typically in the presence of a base such as DMAP and a solvent such as THF to yield the protected intermediate (4), which is reacted with ammonia typically in the presence of a solvent such as methanol, or ethanol or a mixture thereof to yield the carboxylic acid amide (5), which amide (5) is first activated, e.g. by reacting with an organic peroxyacid such as perbenzoic acid or MCPBA and is then reacted with cyclohexanediamine-derivative (6) typically in the presence of a base such as triethylamine and a solvent such as DMF to yield the protected derivative (7), which is reacted with an acid to remove the protecting groups, such as TFA or HCl typically in the presence of a solvent such as dichloromethane or methanol to yield a compound of formula (I), or alternatively the protected derivative (7) is reacted at a low temperature with an acid, e.g. HCl to remove one protecting group and thereafter is reacted with a base, e.g. $NaOCH_3$ to remove the second protecting group to yield a compound of formula (I),

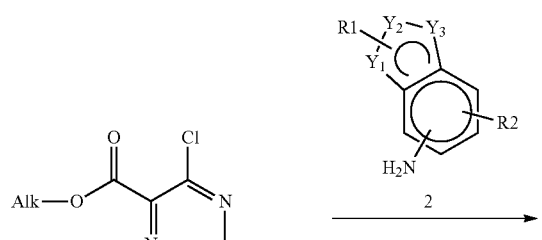

2

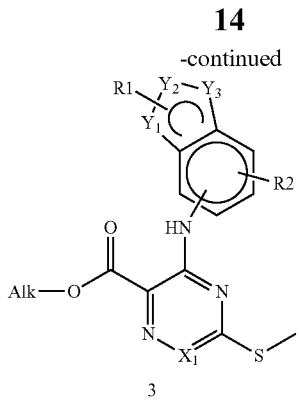

optional Protecting Step, e.g. $(Boc)_2O$

3

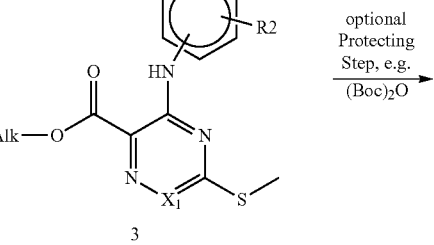

$NH_3$

4

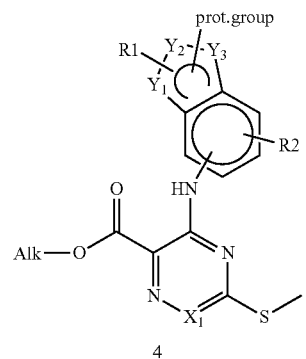

1. peroxyacid
2. 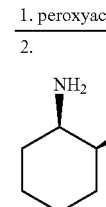

6

5

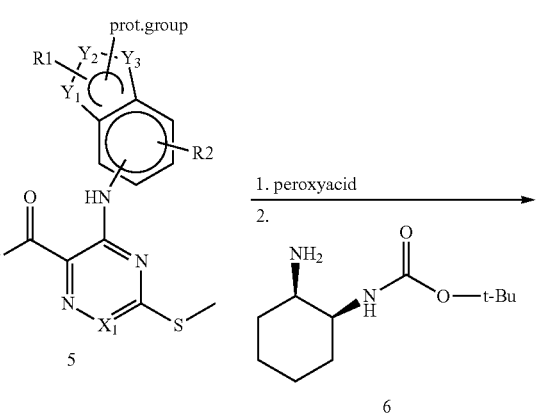

in 1 step, e.g. acid
or
in 2 steps acid/base

7

-continued

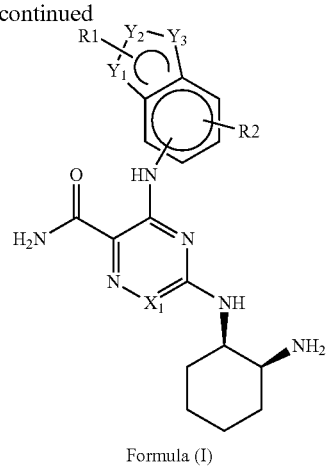

Formula (I)

which may optionally be reacted with an appropriate acid to yield a salt, e.g. a pharmaceutically acceptable salt.

In another embodiment the invention relates to a process of manufacturing a compound of formula (I) or a pharmaceutically acceptable salt thereof, (I)

wherein
X1 is CH;
Y1, Y2 and Y3 are depending on the position of the double bond CH, NH or N, and the bent bond indicates aromaticity of the ring system;
R1 is H, alkyl, CN, or Hal; and
R2 is H, alkyl, or Hal;
wherein in accordance to the scheme shown below,
a carboxylic acid derivative (12), wherein Alk is alkyl and typically is ethyl, is reacted with cyclohexanediamine-derivative (6) typically in the presence of a base such as triethylamine and a solvent such as DMF to yield a derivative (13), which is reacted with intermediate (2) in the presence of a solvent such as dioxane, a base such as K₂CO₃, a paladium salt such as Pd(OAc)₂ and a ligand such as Xantphos to yield an intermediate (15), which is reacted with a metal hydroxide such as LiOH in the presence of solvents such as dioxane and water to yield a carboxylic acid (16), which is activated with an amide coupling reagent such as COMU in the presence of a base such as DIPEA and a solvent such as DMF and subsequently reacted with NH₃ to yield an amide (17), which is reacted with an acid such as HCl to remove the protecting group to yield a compound of formula (I),

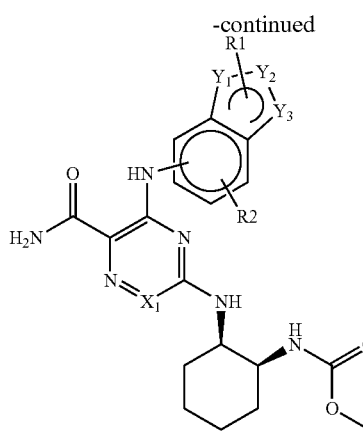

17

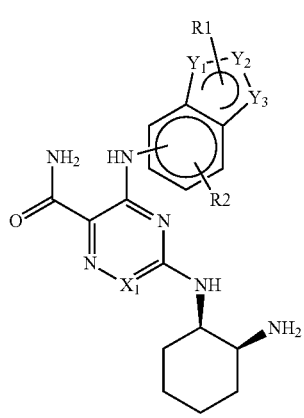

Formula (I)

which may optionally be reacted with an appropriate acid to yield a salt, e.g. a pharmaceutically acceptable salt.

In another embodiment the invention relates to a process of manufacturing a compound of formula (I) or a pharmaceutically acceptable salt thereof,

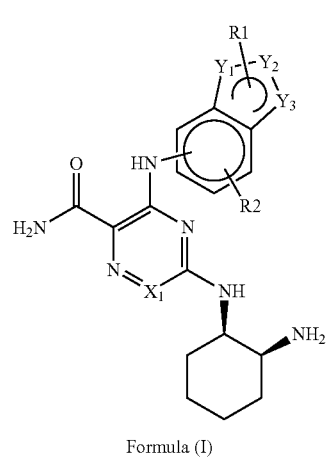

(I)

wherein
X1 is CH;
Y1, Y2 and Y3 are depending on the position of the double bond CH, NH or N, and the bent bond indicates aromaticity of the ring system;
R1 is H, alkyl, CN, or Hal; and
R2 is H, alkyl, or Hal;

wherein in accordance to the scheme shown below, a nitrile derivative (18) is reacted with cyclohexanediamine-derivative (6) typically in the presence of a base such as triethylamine and a solvent such as DMF to yield a derivative (19), which is reacted with an amino-derivative (2) in the presence of a solvent such as dioxane, a base such as $K_2CO_3$, a paladium salt such as $Pd(OAc)_2$ and a ligand such as Xantphos to yield an intermediate (20), which is reacted with with a metalhydroxide such as NaOH and $H_2O_2$ in the presence of solvents such as DMSO and EtOH to yield an amide (21) which is which is reacted with an acid such as HCl to remove the protecting group to yield a compound of formula (I),

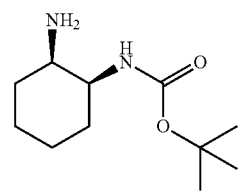

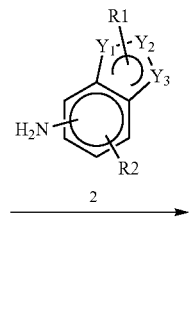

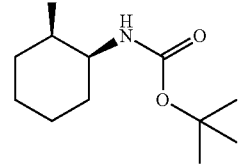

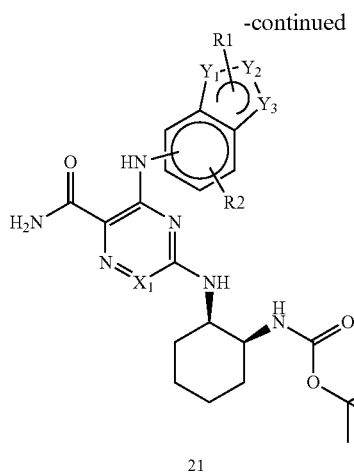

which may optionally be reacted with an appropriate acid to yield a salt, e.g. a pharmaceutically acceptable salt.

EXPERIMENTAL SECTION

1. Analytical Methods

Liquid Chromatography:
UPLC/MS: Waters Acquity UPLC+Waters ZQ2000 MS
UV-PDA: 210-450 nM
MS range: 100-1200 Da
Column: Acquity HSS T3 2.1×50 mm 1.8μ at 60° C.
Mobile phase:
A: water+0.05% formic acid
B: acetonitrile+0.04% formic acid

| Time [minutes] | Flow [ml/min] | A [%] | B [%] |
|---|---|---|---|
| 0.00 | 1.000 | 95 | 5 |
| 1.40 | 1.000 | 2 | 98 |
| 1.80 | 1.000 | 2 | 98 |
| 1.90 | 1.000 | 95 | 5 |
| 2.00 | 1.000 | 95 | 5 |

2. Preparative HPLC

Column: Waters SunFire 30×100 mm, C18, 5 μm
Flow: 20 ml/min
Solvent: Acetonitril/water/0.1% TFA (gradient)

ABBREVIATIONS

Boc2O: Di-t-butyl dicarbonate
COMU: (1-Cyano-2-ethoxy-2-oxoethylidenaminooxy)dimethylamino-morpholino-carbenium hexafluorophosphate
DIPEA: N,N-Diisopropylethylamine
DMAP: 4-Dimethylaminopyridine
DMF: Dimethylformamide
DMSO: Dimethylsolfoxide
HPLC: High Pressure Liquid Chromatography
MCPBA: meta-Chloroperoxybenzoic acid
NMP: N-Methyl-2-pyrrolidon
TFA: Trifluoroacetic acid
THF: Tetrahydrofuran
UPLC: Ultra Performance Liquid Chromatography
Xantphos: 4,5-Bis(diphenylphosphino)-9,9-dimethylxanthene To the extent compounds are mentioned as such in a reaction scheme and/or within the full experimental part, such a compound is either commerically available or if not, has been fully described in the prior art, and hence can be obtained accordingly for carrying out a corresponding reaction step.

Example 1.1

3-((1R,2S)-2-Amino-cyclohexylamino)-5-(1H-indol-7-ylamino)-[1,2,4]triazine-6-carboxylic acid amide

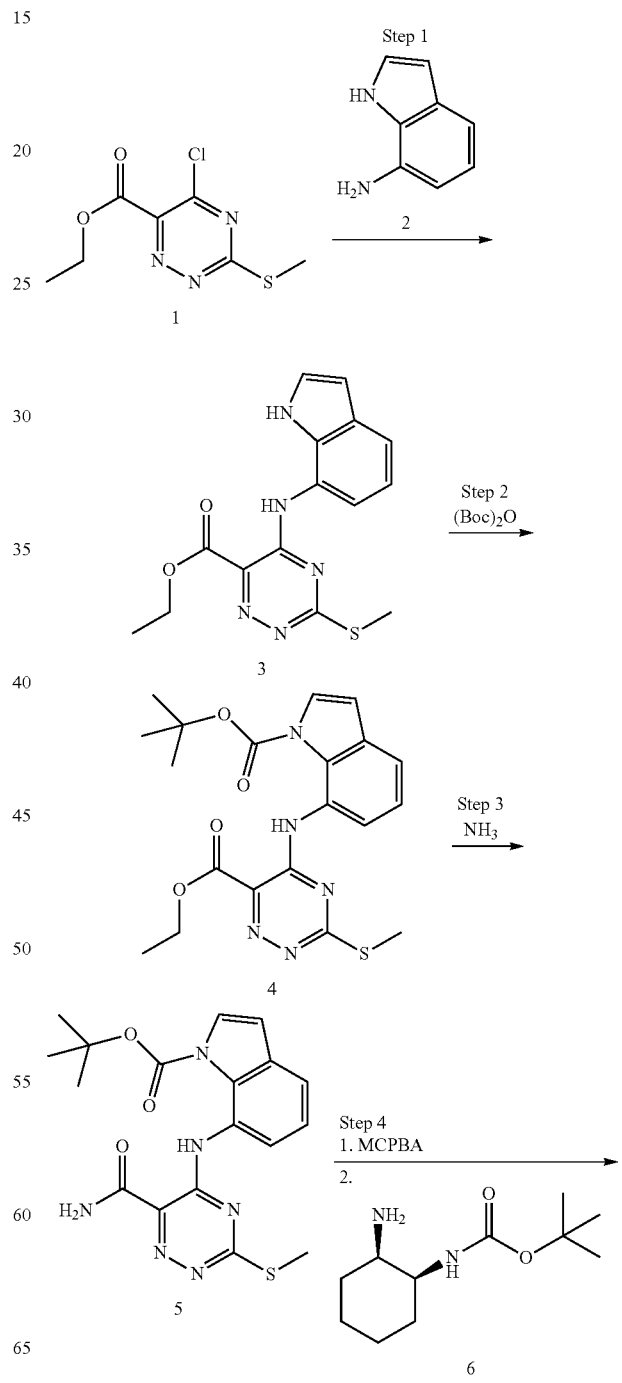

-continued

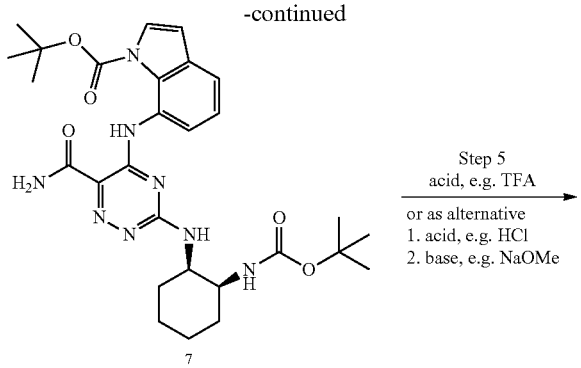

7

Step 5
acid, e.g. TFA
or as alternative
1. acid, e.g. HCl
2. base, e.g. NaOMe

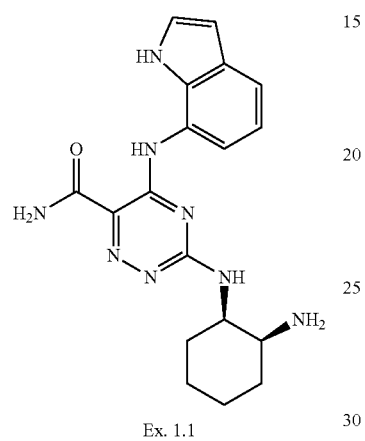

Ex. 1.1

Step 1: The indole-compound 2 (283 mg) was added to a solution of 1 (500 mg) in NMP (2 mL) and the mixture stirred at 25° C. for 15 min. The mixture was added to water, the precipitate collected and dried to give compound 3 (660 mg) as a beige solid. UPLC/MS found for C15H15N5O2S as (M+H)+ 329.9; UPLC retention time 1.07 min.

Step 2: To a suspension of 3 (660 mg) and DMAP (22.5 mg) in THF (4 mL) was added at 0° C. a solution of (Boc)$_2$O in THF (3 mL). The mixture was stirred at 25° C. for 30 min. The solvent was removed and the residue purified by chromatography on silica (gradient cyclohexane/ethyl acetate) to give compound 4 (555 mg) as a yellow solid. UPLC/MS found for C20H23N5O4S as (M+H)+ 430.0; UPLC retention time 1.28 min.

Step 3: A mixture of 4 (260 mg) and NH$_3$ (2 mL of a 7 molar solution in methanol) was stirred at 25° C. for 45 min. The mixture was added to ice water, the precipitate collected and dried to give compound 5 (183 mg). UPLC/MS found for C18H20N6O3S as (M+H)+401.0; UPLC retention time 1.09 min.

Step 4: To a solution of 5 (180 mg) in DMF (2 mL) was added MCPBA (199 mg) at 0° C. and the mixture stirred for 45 min. NEt$_3$ (0.31 mL) and 6 (95 mg) were added and the mixture stirred at 65° C. for 15 min. The solvent was removed and the residue purified by HPLC to give compound 7 (222 mg) as a yellow solid. UPLC/MS found for C28H38N8O5 as (M+H)+ 567.2; UPLC retention time 1.13 min.

Step 5: A solution of 7 (222 mg) in CH$_2$Cl$_2$ (2 mL), TFA (2 mL) and water (0.02 mL) was stirred at 25° C. for 0.5 h. Then the mixture was kept for 16 h at 0° C. and for 1 h at 25° C. The solvents were evaporated and the residue purified by HPLC. Product was dissolved in CH$_2$Cl$_2$ and extracted with aqueous NaOH to give Example 1.1 (62 mg) as a yellow solid. $^1$H-NMR (400 MHz; CD3OD, 25° C.): 7.52 (1H, d); 7.23 (1H, d); 7.16 (1H, d); 7.04 (1H, t); 6.51 (1H, d); 3.58 (1H, m); 2.82 (1H, m); 1.75-1.15 (8H, m); UPLC/MS found for C18H22N8O as (M+H)+367.1; UPLC retention time 0.64 min.

Alternative Step 5:

Step 5.1: To a solution of compound 7 (4.56 g) in a mixture of CH$_2$Cl$_2$ (400 ml) and MeOH (40 ml) was added dropwise a solution of HCl in dioxan (40.2 ml, 4 N) at 0° C. and the mixture stirred for 16 h at 25° C. The mixture was diluted with CH$_2$Cl$_2$ and washed with bicarbonate solution. The aqueous solution was extracted with CH$_2$Cl$_2$ and the combined organic phases washed with brine. The organic phase was passed through a phase-separating column containing a short bed of Na$_2$SO$_4$ and the solvend removed to give a yellow solid, i.e. compound 7a which was used without further purification in the next step. UPLC/MS found for C18H22N8O as (M+H)+ 467.1; UPLC retention time 0.77 min.

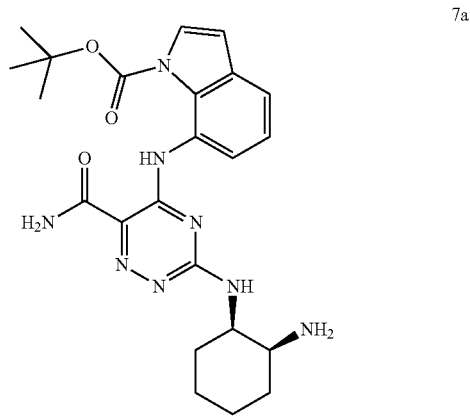 [SMILES: CC(C)(C)OC(=O)n1ccc2cccc(Nc3nc(N[C@@H]4CCCC[C@@H]4N)nnc3C(N)=O)c21]

7a

Step 5.2: To a solution of compound 7a (3.48 g) in a mixture of THF (120 ml) and MeOH (50 ml) was added within 15 min a solution of NaOMe in MeOH (8.29 ml, 5.4 N) at 25° C. and the mixture stirred for 3 h. The mixture was diluted with ethyl acetate and washed with water. The aqueous solution was extracted with ethyl acetate and the combined organic phases washed with bicarbonate solution followed by brine. The organic phase was passed through a phase-separating column and the solvend removed to give a yellow solid. The crude material was purified using a Biotage KP-NH column (0-10% MeOH in ethyl acetate) to give Example 1.1. (1.90 g) as a yellow solid. $^1$H-NMR, and UPLC/MS see data provided under step 5.

Accordingly, in another embodiment the invention relates to a process of manufacturing a compound of formula (II), as shown in the scheme below, wherein X1 is N and the additional variables are as defined hereinbefore, e.g. as in claim 1, and wherein Alk stands for alkyl as defined hereinbefore, especially C1-C4alkyl, wherein a carboxylic acid derivative (1), wherein Alk typically is ethyl, is reacted with a 7-amino-indole derivative (2) to yield indole intermediate (3) the free amino group of which is then protected in a protecting step, e.g. by reacting indole-derivative (3) e.g. with a protecting agent such as BOC$_2$O typically in the presence of a base such as DMAP and a solvent such as THF to yield the protected indole (4), which is reacted with ammonia typically in the presence of a solvent such as methanol, or ethanol or a mixture thereof to yield the carboxylic acid amide (5), which amide (5) is first activated, e.g. by reacting with an organic peroxyacid such as perbenzoic acid or MCPBA and is then reacted with cyclohexanediamine-derivative (6) typically in the presence of a base such as triethylamine and a solvent such as DMF to yield the protected derivative (7), which is reacted with an acid to remove the protecting groups, such as TFA or HCl typically in the presence of a solvent such as dichloromethane or methanol to yield a compound of formula (II), or alternatively the protected derivative (7) is first reacted with an acid, typically HCl, generally in the presence of a solvent, e.g. dioxin, THF, or ethanol or the like and typically at a temperature below room temperature, typically at 0° C. to yield an intermediate carrying only one protecting group, which intermediate is then reacted with a base, e.g. NaOMe generally in the presence of a solvent, e.g. methanol to yield the final compound of formula (II), which may be optionally reacted with an appropriate acid to furnish a salt, especially a pharmaceutically acceptable salt.

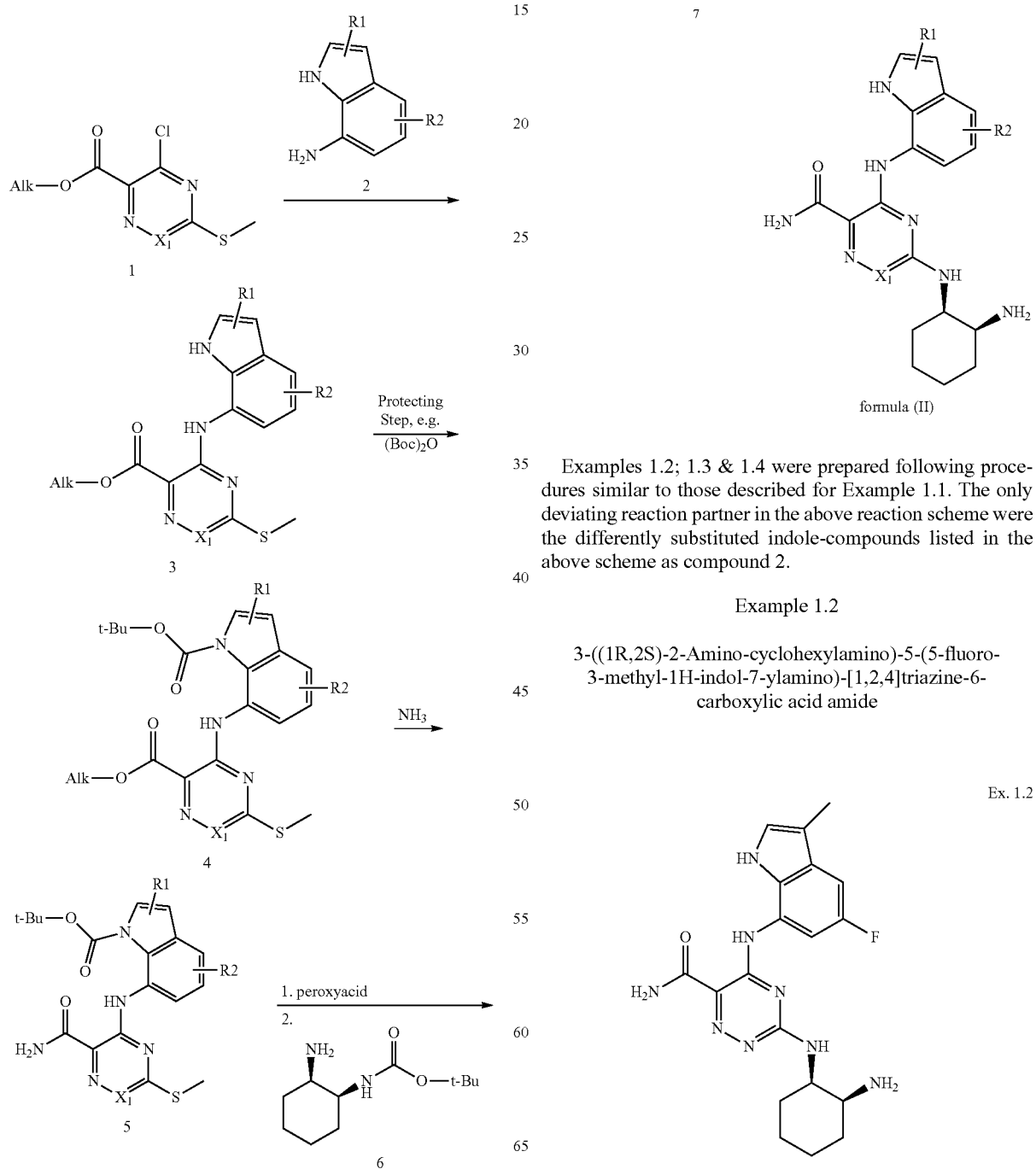

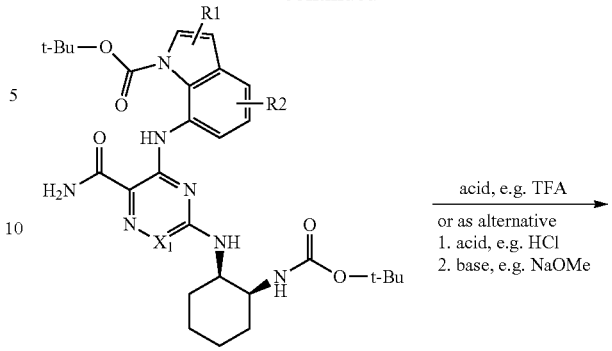

Examples 1.2; 1.3 & 1.4 were prepared following procedures similar to those described for Example 1.1. The only deviating reaction partner in the above reaction scheme were the differently substituted indole-compounds listed in the above scheme as compound 2.

Example 1.2

3-((1R,2S)-2-Amino-cyclohexylamino)-5-(5-fluoro-3-methyl-1H-indol-7-ylamino)-[1,2,4]triazine-6-carboxylic acid amide Ex. 1.2

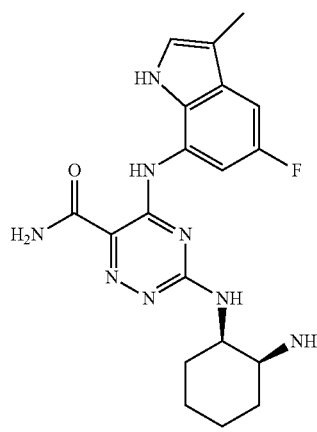

This compound was obtained by taking in reaction step 2 the reaction partner 3-methyl-5-fluoro-7-amino-indole. Upon purification via HPLC the compound had been characterized:

$^1$H-NMR (400 MHz; CD$_3$OD, 25° C.): 7.27 (1H, m); 7.10 (2H, m), 3.70 (1H, m); 3.00 (1H, m); 2.30 (3H, s); 1.70-1.25 (8H, m); UPLC/MS found for C19H23FN8O as (M+H)$^+$ 399.1; UPLC retention time 0.69 min.

Preparation of 3-methyl-5-fluoro-7-amino-indole

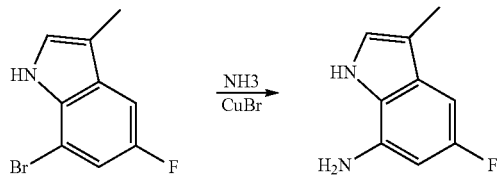

A mixture of 7-Bromo-5-fluoro-3-methyl-indole (2.5 g), Cu (0.77 g), CuBr (1.57 g) and NH$_3$ (30 mL of a 33% aqueous solution) was heated in an autoclave for 2 h at 170° C. The mixture was diluted with water and extracted with ethyl acetate. The organic phase was dried and the solvent removed to give 3-methyl-5-fluoro-7-amino-indole (1.84 g) as an oil which was used without further purification. UPLC/MS found for C9H9FN2 as (M+H)$^+$ 165.2

Example 1.3

3-((1R,2S)-2-Amino-cyclohexylamino)-5-(3-methyl-1H-indol-7-ylamino)-[1,2,4]triazine-6-carboxylic acid amide

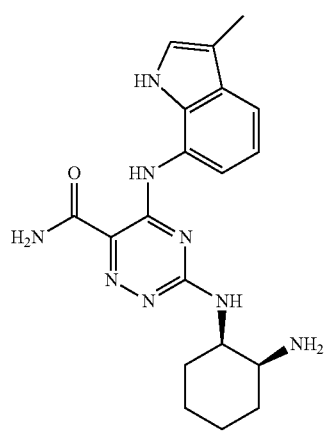

Ex. 1.3

This compound was obtained by taking in reaction step 2 the reaction partner 3-methyl-7-amino-indole. Upon purification via HPLC the compound had been characterized:

$^1$H-NMR (400 MHz; DMSO-d$_6$, 100° C.): 10.78 (1H, s); 10.14 (1H, s); 7.34 (1H, d); 7.23 (1H, d); 7.00 (1H, s); 6.96 (1H, t); 3.66 (1H, m); 2.95 (1H, m); 2.27 (3H, s); 1.90-1.55 (8H, m); UPLC/MS found for C19H24N8O as (M+H)$^+$ 381.1; UPLC retention time 0.63 min.

Example 1.4

3-((1R,2S)-2-Amino-cyclohexylamino)-5-(1H-indol-4-ylamino)-[1,2,4]triazine-6-carboxylic acid amide

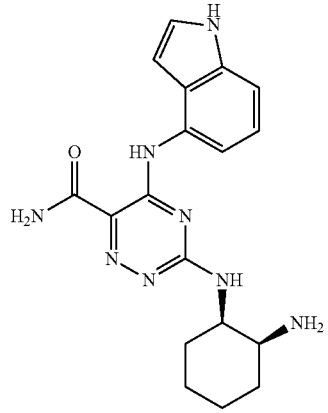

Ex. 1.4

This compound was obtained by taking in reaction step 2 the reaction partner 4-amino-indole. Upon purification via HPLC the compound had been characterized:

$^1$H-NMR (400 MHz; CD$_3$OD, 25° C.): 7.58 (1H, d); 7.45 (1H, d); 7.43 (1H, d); 7.23 (1H, t); 6.63 (1H, d); 4.40 (1H, m); 3.70 (1H, m); 2.00-1.55 (8H, m); UPLC/MS found for C18H22N8O as (M+H)$^+$ 367.0; UPLC retention time 0.52 min.

Example 2.1

3-((1R,2S)-2-Amino-cyclohexylamino)-5-(1-methyl-1H-indazol-4-ylamino)-[1,2,4]triazine-6-carboxylic acid amide

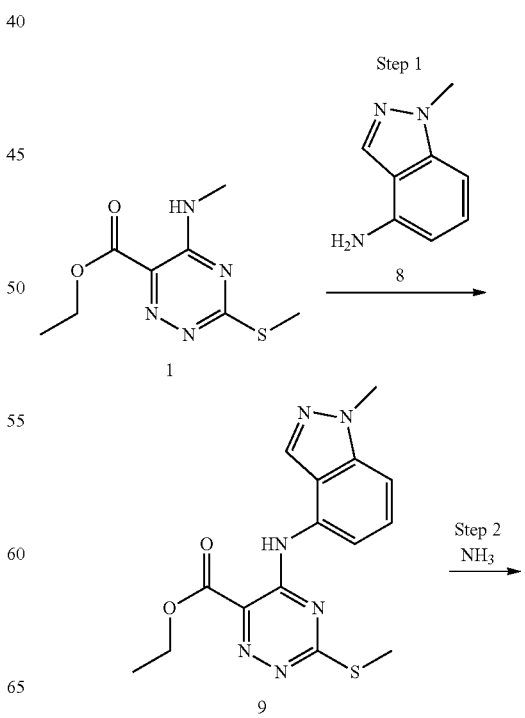

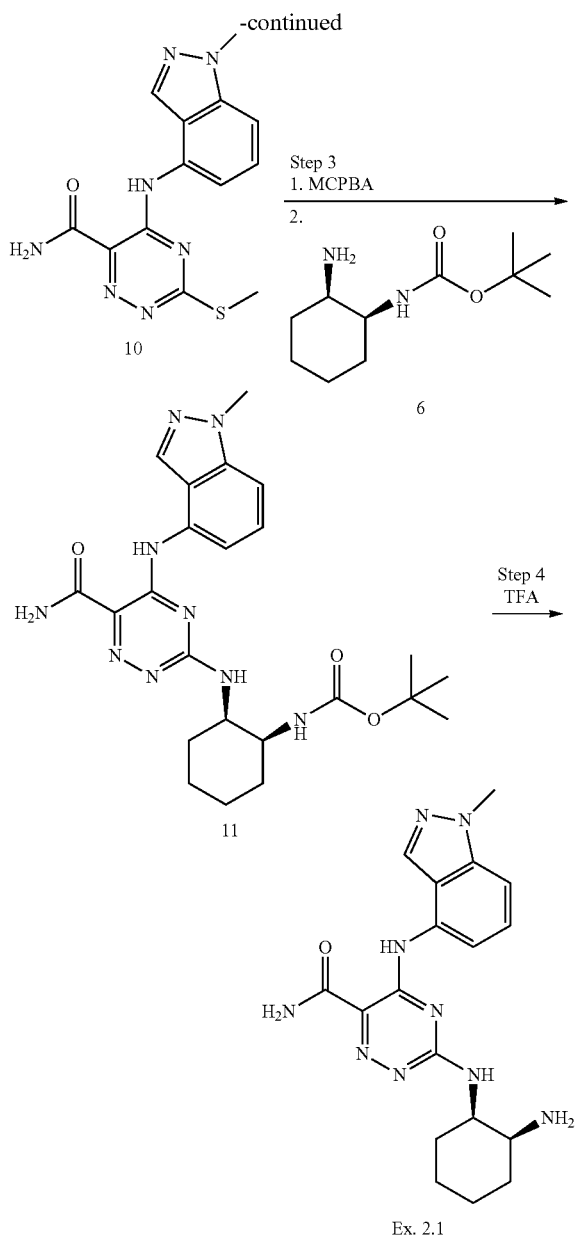

Step 1: At 0° C. compound 8 (283 mg) was added to a solution of 1 (300 mg) in NMP (2 mL) and the mixture was stirred for 10 min. Stirring was continued for 45 min at 25° C. Methanol (3 mL) was added, the precipitate collected and dried to give compound 9 (389 mg) as a yellow solid. UPLC/MS found for C15H16N6O2S as (M+H)+ 345.1; UPLC retention time 0.99 min.

Step 2: A mixture of 9 (362 mg) and NH3 (5 mL of a 7 molar solution in methanol) was stirred at 45° C. for 45 min. The precipitate was collected and dried to give compound 10 (329 mg). UPLC/MS found for C13H13N7OS as (M+H)+ 316.0; UPLC retention time 0.86 min.

Step 3: At 0° C. MCPBA (448 mg) was added to a solution of 10 (315 mg) in DMF (5 mL) and the mixture stirred for 45 min. DMF (5 ml) was added in portions while stirring was continued for 1.5 h at 45° C. NEt3 (0.697 mL) and 6 (236 mg) were added and the mixture stirred for 20 h at 25° C. The mixture was added to water, the precipitate collected and dried to give 11 (409 mg) as an orange solid. UPLC/MS found for C23H31N9O3 as (M+H)+ 482.1; UPLC retention time 0.96 min.

Step 4: A mixture of 11 (409 mg), CH2Cl2 (5 mL), TFA (1.0 mL) and water (0.01 mL) was stirred at 25° C. for 1 h. The solvents were removed and the residue purified by HPLC. The TFA salt of Example 2.1 was passed through an Isolute SCX-2 column to yield the free base of Example 2.1 (37 mg) as a yellow solid. 1H-NMR (400 MHz; DMSO-d6, 100° C.): 11.84 (1H, s); 8.02 (1H, d); 7.97 (1H, s); 7.38 (1H, t), 7.33 (1H, d); 4.05 (3H, s); 3.95 (1H, m); 3.15 (1H, m); 1.75-1.25 (8H, m); UPLC/MS found for C18H23N9O as (M+H)+ 382.1; UPLC retention time 0.56 min.

Examples 2.2-2.6 were prepared following procedures similar to those described for Example 2.1.

Example 2.2

3-((1R,2S)-2-Amino-cyclohexylamino)-5-(2-methyl-2H-indazol-4-ylamino)-[1,2,4]triazine-6-carboxylic acid amide

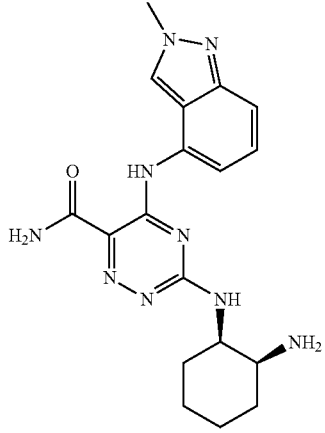

In the synthesis of example 2.2, the reaction partner 8, i.e. 1-methyl-4-amino-1H-indazol, was replaced by 2-methyl-4-amino-2H-indazol. Upon purification via HPLC, the compound was characterized:

1H-NMR (400 MHz; DMSO-d6, 100° C.): 11.57 (1H, s); 8.18 (1H, s), 7.81 (1H, d); 7.31 (1H, d); 7.19 (1H, t); 4.18 (3H, s); 3.92 (1H, m); 3.13 (1H, m); 1.75-1.30 (8H, m); UPLC/MS found for C18H23N9O as (M+H)+ 382.1; UPLC retention time 0.52 min.

Example 2.3

3-((1R,2S)-2-Amino-cyclohexylamino)-5-(3-chloro-1H-indol-7-ylamino)-[1,2,4]triazine-6-carboxylic acid amide

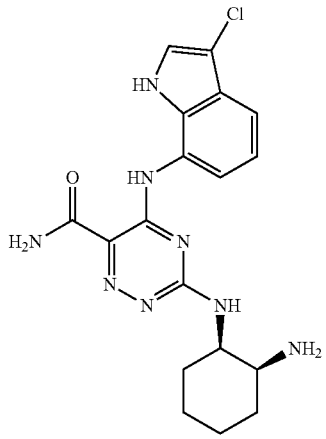

In the synthesis of example 2.3, the reaction partner 8 in the above scheme, i.e. 1-methyl-4-amino-1H-indazol, was replaced by 3-chloro-7-amino-1H-indole. Upon purification via HPLC, the compound was characterized:

$^1$H-NMR (400 MHz; CD$_3$OD, 25° C.): 7.50 (1H, d); 7.28 (1H, s), 7.27 (1H, d); 7.25 (1H, t); 3.50 (1H, m); 2.82 (1H, m); 1.70-1.15 (8H, m); UPLC/MS found for C18H21ClN8O as (M+H)$^+$ 401.0; UPLC retention time 0.67 min.

Example 2.4

3-((1R,2S)-2-Amino-cyclohexylamino)-5-(3-cyano-1H-indol-7-ylamino)-[1,2,4]triazine-6-carboxylic acid amide

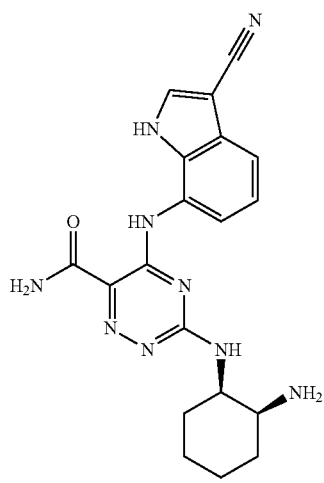

Ex. 2.4

In the synthesis of example 2.4, the reaction partner 8 in the above scheme, i.e. 1-methyl-4-amino-1H-indazol, was replaced by 3-cyano-7-amino-1H-indole. Upon purification via HPLC, the compound was characterized:

$^1$H-NMR (400 MHz; CD$_3$OD, 25° C.): 7.99 (1H, s); 7.62 (1H, m), 7.31 (2H, m); 3.40 (1H, m); 2.78 (1H, m); 1.70-1.10 (8H, m); UPLC/MS found for C19H21N9O as (M+H)$^+$ 392.0; UPLC retention time 0.58 min.

Example 2.5

3-((1R,2S)-2-Amino-cyclohexylamino)-5-(1H-indazol-4-ylamino)-[1,2,4]triazine-6-carboxylic acid amide

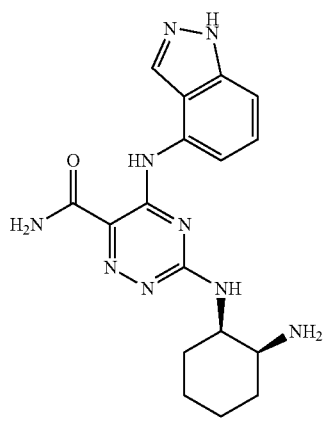

Ex. 2.5

In the synthesis of example 2.5, the reaction partner 8 in the above scheme, i.e. 1-methyl-4-amino-1H-indazol, was replaced by 4-amino-1H-indazole. Upon purification via HPLC, the compound was characterized:

$^1$H-NMR (400 MHz; DMSO-d$_6$, 100° C.): 11.82 (1H, s); 8.02 (1H, s), 7.96 (1H, d); 7.31 (2H, m), 7.33 (1H, d); 4.01 (1H, m); 3.24 (1H, m); 1.75-1.30 (8H, m); UPLC/MS found for C17H21N9O as (M+H)$^+$ 368.1; UPLC retention time 0.50 min.

Example 2.6

3-((1R,2S)-2-Amino-cyclohexylamino)-5-(5-fluoro-1H-indol-7-ylamino)-[1,2,4]triazine-6-carboxylic acid amide

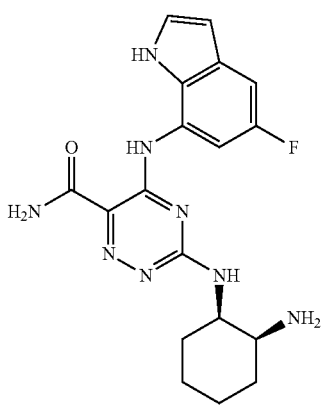

Ex. 2.6

In the synthesis of example 2.6, the reaction partner 8 in the above scheme, i.e. 1-methyl-4-amino-1H-indazol, was replaced by 5-fluoro-7-amino-1H-indole. Upon purification via HPLC, the compound was characterized:

$^1$H-NMR (400 MHz; CD$_3$OD, 25° C.): 7.32 (1H, d); 7.25 (1H, m), 7.18 (1H, m); 6.50 (1H, d); 3.67 (1H, m); 2.93 (1H, m); 1.70-1.25 (8H, m); UPLC/MS found for C18H21FN8O as (M+H)$^+$ 385.1; UPLC retention time 0.61 min.

Preparation of 5-fluoro-7-amino-indole

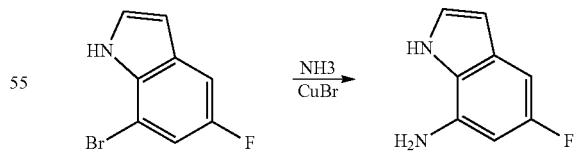

A mixture of 7-Bromo-5-fluoro-indole (1 g), Cu (0.31 g), CuBr (0.64 g) and NH$_3$ (30 mL of a 33% aqueous solution) was heated in an autoclave for 1.5 h at 155° C. The mixture was diluted with water and extracted with ethyl acetate. The organic phase was dried and the solvent removed to give 5-fluoro-7-amino-indole (0.67 g) as an oil which was used without further purification. UPLC/MS found for C8H7FN2 as (M+H)$^+$ 151.0.

Example 3.1

5-((1R,2S)-2-Amino-cyclohexylamino)-3-(1-methyl-1H-indol-4-ylamino)-pyrazine-2-carboxylic acid amide

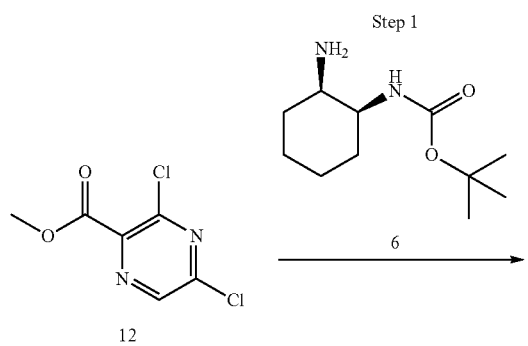

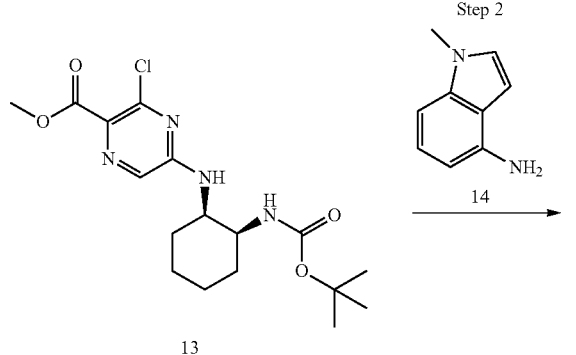

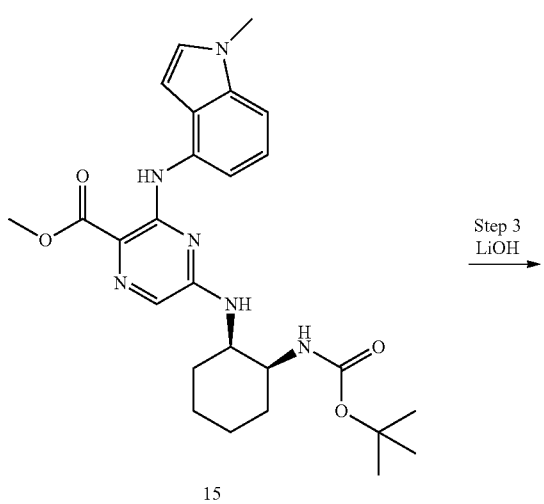

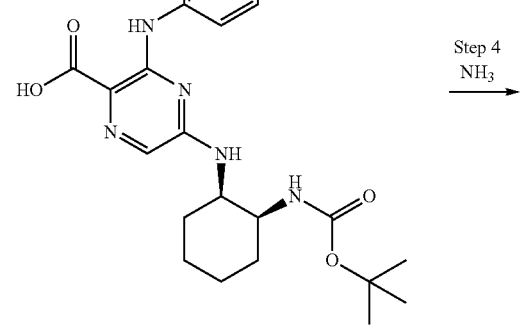

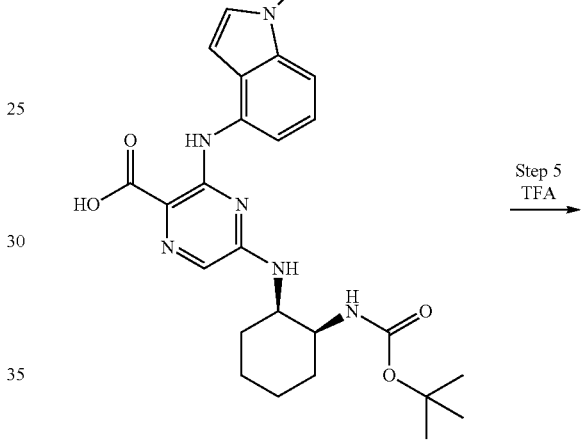

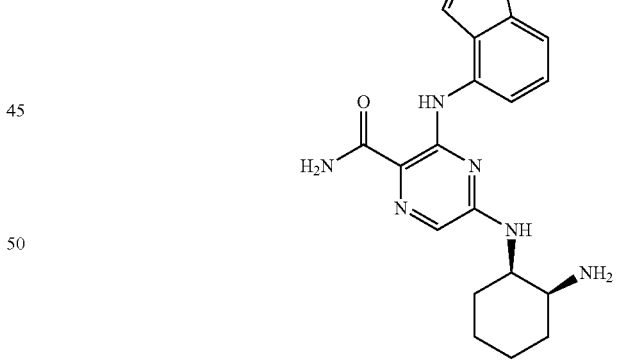

Step 1: At 0° C. a solution of 12 (2.59 g) and NEt$_3$ (1.744 ml) in DMF (20 ml), was added to a solution of 6 (2.95 g) in DMF (5 ml) and stirred for 16 h at 25° C. The mixture was diluted with ethyl acetate (70 ml) and washed with water (50 ml). The aqueous phase was extracted with ethyl acetate (30 ml), the combined organic phases washed with brine, dried over Na$_2$SO$_4$ and the solvent evaporated. Chromatography on silica (gradient cyclohexane/ethyl acetate) gave 13 (950 mg) as a yellow solid. UPLC/MS found for C17H25ClN4O4 as (M+1)$^+$ 385.0, UPLC retention time 1.03 min.

Step 2: To a solution of 13 (300 mg) in dioxan (2 ml) was added under argon at 25° C. 14 (171 mg), K$_2$CO$_3$ (1077 mg), Pd(OAc)$_2$ (1.75 mg) and Xantphos (9.02 mg). The mixture was heated at 90° C. for 16 h. The mixture was diluted with ethyl acetate (30 ml) and washed with 0.1N HCl (30 ml). The aqueous phase was extracted with Ethyl acetate (20 ml), the combined organic phases washed with bicarbonate solution and brine. The mixture was dried over Na$_2$SO$_4$ and the solvent removed. Chromatography on silica (gradient cyclohexane/ ethyl acetate) gave 15 (242 mg, 62.8%). UPLC/MS found for C26H34N6O4 as (M+1)$^+$495.1; UPLC retention time 1.29 min.

Step 3: To a solution of 15 (242 mg, 0.489 mmol) in dioxan (1 ml) was added LiOH (82 mg) and water (0.5 ml). The mixture was stirred for 16 h at 25° C., diluted with ethyl acetate (30 ml), acidified with 0.1N HCl and extracted with ethyl acetate (20 ml). The organic phase was washed with brine, dried over Na$_2$SO$_4$ and evaporated to dryness to give 16 (189 mg, 80%). UPLC/MS found for C25H32N6O4 as (M+1)$^+$=481.1; UPLC retention time 1.20 min.

Step 4: To a solution of 16 (189 mg) in DMF (2 ml) was added DIPEA (0.069 ml) followed by COMU (185 mg) and the resultant mixture stirred for 5 min at 25° C. Ammonium hydroxide (0.337 ml of 25% aqueous solution) and DIPEA (0.069 ml) were added and stirring continued for 30 min. The mixture was diluted with ethyl acetate (20 ml), washed with bicarbonate solution (20 ml), dried and the solvent removed to give 17 (154 mg). UPLC/MS found for C25H33N7O3 as (M+H)$^+$ 480.1; UPLC retention time 1.17 min.

Step 5: To a solution of 17 (154 mg) in CH$_2$Cl$_2$ (10 ml) and MeOH (1 ml) was added TFA (0.495 ml) and the mixture stirred for 16 h at 25° C. The mixture was diluted with ethyl acetate (20 ml), washed with bicarbonate solution (20 ml) and dried. Most of the solvent was removed, cyclohexane was added and the precipitate collected. Example 3.1 was (103 mg) was isolated as a yellow-brown solid. $^1$H-NMR (400 MHz; DMSO-d$_6$, 100° C.): 11.85 (1H, s); 8.17 (1H, m); 7.72 (1H, m); 7.47 (1H, s); 7.41 (1H, m); 7.31 (1H, d); 7.24 (1H, m); 7.95 (2H, m); 6.51 (1H, d); 3.97 (1H, m); 3.79 (3H, s); 3.02 (1H, m); 1.80-1.30 (8H, m); UPLC/MS found for C20H25N7O as (M+H)$^+$=380.1; UPLC retention time 0.71 min.

Example 4.1

5-((1R,2S)-2-Amino-cyclohexylamino)-3-(1H-indol-7-ylamino)-pyrazine-2-carboxylic acid amide

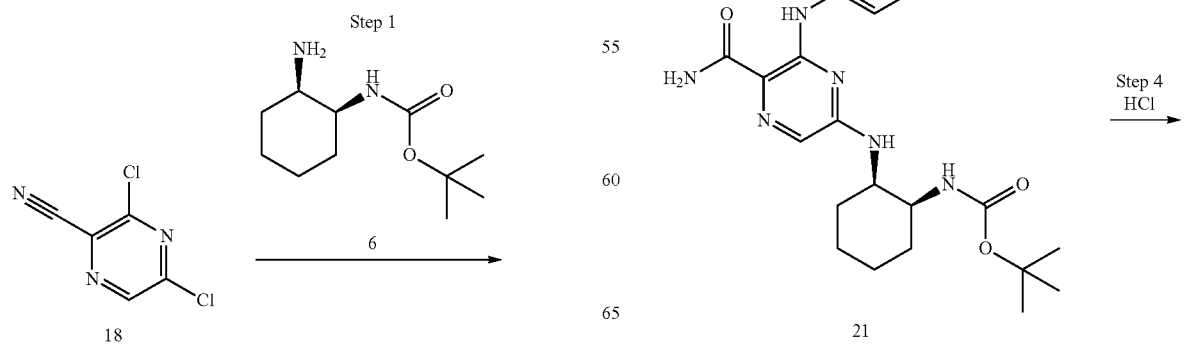

-continued

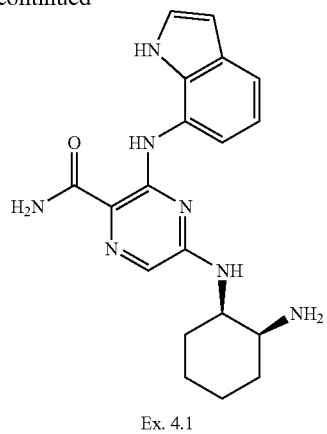

Ex. 4.1

Step 1: At 0° C. 6 (739 mg) in DMF (2 ml) was added to a solution of 18 (500 mg) and NEt₃ (0.401 ml, 2.87 mmol) in DMF (5 ml) and the mixture stirred for 16 h at 25° C. The mixture was diluted with ethyl acetate (50 ml) and washed with water (50 ml). The aqueous was extracted with ethyl acetate (30 ml), the combined organic phases washed with brine, dried over Na₂SO₄ and the solvent removed. Chromatography on silica (gradient cyclohexane/ethyl acetate) gave 19 (905 mg) as a colorless solid. UPLC/MS found for C16H22ClN5O2 as (M+H)⁺ 352.0; UPLC retention time 1.13 min.

Step 2: To 19 (300 mg) in dioxan (2 ml) was added under argon 2 (135 mg), K₂CO₃ (1178 mg), Pd(OAc)₂ (1.91 mg) and Xantphos (9.9 mg,). The mixture was stirred for 16 h at 90° C. The mixture was diluted with ethyl acetate (20 ml), washed with HCl (0.1N; 30 ml). The aqueous phase was extracted with ethyl acetate (20 ml), the combined organic phases washed with bicarbonate solution and brine, dried over Na₂SO₄ and the solvent removed. Chromatography on silica (gradient cyclohexane/ethyl acetate) gave 20 (368 mg). UPLC/MS found for C24H29N7O2 as (M+H)⁺ 448.1; UPLC retention time 1.19 min.

Step 3: To 20 (368 mg) in DMSO (2 ml) and EtOH (4 ml) was added at 0° C. NaOH (1.03 ml) and H₂O₂ (0.382 ml). After stirring for 2 h at 25° C. the mixture was partitioned between water and Ethyl acetate (30 ml each). The organic phase was washed with bicarbonate solution and brine, dried over Na₂SO₄ and the solvent removed to give crude 21 (320 mg) which was used without further purification in the next step. UPLC/MS found for C24H31N7O3 (M+H)⁺ 466.1; UPLC retention time 1.18 min.

Step 4: To 21 (320 mg) in CH₂Cl₂ (20 ml) and MeOH (4 ml) was added HCl (4N; 3.44 ml) and the mixture stirred for 16 h at 25° C. The mixture was diluted with CH₂Cl₂ (50 ml) and washed with bicarbonate solution and brine, dried with Na₂SO₄ and the solvent removed. Chromatography using a KP-NH column (gradient MeOH/ethyl acetate gradient) gave Example 4.1 (74 mg) as a yellow solid. ¹H-NMR (400 MHz; DMSO-d₆, 25° C.): 11.04 (1H, s); 10.71 (1H, s); 7.67 (1H, m); 7.42 (1H, s); 7.32 (1H, d); 7.28 (1H, d); 7.24 (1H, m); 7.22 (1H, m); 7.18 (1H, m); 6.93 (1H, t); 6.44 (1H, m); 3.65 (1H, m); 2.87 (1H, m); 1.55-1.03 (8H, m); UPLC/MS found for C19H23N7O (M+H)⁺ 366.1; UPLC retention time 0.65 min.

Example 4.2 was prepared following procedures similar to those described for Example 4.1, i.e. in reaction step 2,7-amino-1H-indole was replaced by 3-methyl-7-amino-1H-indole.

Example 4.2

5-((1R,2S)-2-Amino-cyclohexylamino)-3-(3-methyl-1H-indol-7-ylamino)-pyrazine-2-carboxylic acid amide

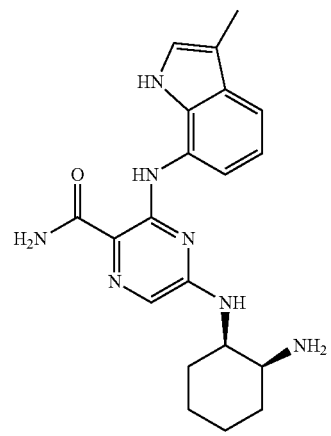

Ex. 4.2

¹H-NMR (400 MHz; DMSO-d₆, 25° C.): 11.06 (1H, s); 10.35 (1H, s); 7.67 (1H, m); 7.42 (1H, s); 7.33 (1H, d); 7.25 (1H, m); 7.24 (1H, d); 7.17 (1H, m); 7.02 (1H, m); 6.92 (1H, t); 3.66 (1H, m); 2.88 (1H, m); 2.26 (3H, s); 1.60-1.08 (8H, m); UPLC/MS found for C20H25N7O as (M+H)⁺=380.1; UPLC retention time 0.71 min.

Biopharmaceutical Part

The compounds of the invention in free form or in pharmaceutically acceptable salt form, exhibit valuable pharmacological properties as described in the tests below, e.g. in vitro and in vivo tests, and are therefore indicated for therapy.

Syk Enzyme Assay

A number of compounds of the present invention were assayed in a chip based microfluidic mobility shift assay. All assays were performed in 384 well microtiter plates. Each assay plate contained 8-point serial dilutions for 40 test compounds, as well as four 8-point serial dilutions of staurosporine as reference compound, plus 16 high- and 16 low controls. Liquid handling and incubation steps were done on a Thermo CatX workstation equipped with a Innovadyne Nanodrop Express. Between pipetting steps, tips were cleaned in wash cycles using wash buffer. The assay plates were prepared by addition of 50 nl per well of compound solution in 90% DMSO. The kinase reactions were started by stepwise addition of 4.5 µl per well of peptide/ATP-solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 1 mM MgCl₂, 3 mM MnCl₂, 4 µM ATP, 4 µM peptide (5-Fluo-Ahx-GAPDYENLQELNKK-Amid) (purchased from Biosyntan, Berlin, Germany) and 4.5 µl per well of enzyme solution (50 mM HEPES, pH 7.5, 1 mM DTT, 0.02% Tween20, 0.02% BSA, 0.6% DMSO, 10 mM beta-glycerophosphate, and 10 µM sodium orthovanadate, 1 mM MgCl₂, 3 mM MnCl₂, 4 nM Syk (Syk(2-635) (UniProtKB/Swiss-Prot: KSYK_HUMAN, P43405), produced inhouse from insect cells). Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96 well plates. This format enabled the assay of maximally 40 individual test compounds at 8 concentrations (single points) including 4 reference compounds. The dilution protocol included the production of "pre-dilution plates", "master plates" and "assay plates".

Pre-Dilution Plates:

96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master Plates:

30 µL of individual compound dilutions including standard compound and controls of the 4 "pre-dilution plates" were transferred into a 384 "master plate" including the following concentrations 1'810, 362, 72.5, 54.6, 14.5, 2.9, 0.58 and 0.12 µM, respectively in 90% of DMSO.

Assay Plates:

Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 9.05 µL. This led to a final compound concentration of 10, 2.0, 0.4, 0.08, 0.016, 0.0032, 0.00064 and 0.000128 µM and a final DMSO concentration of 0.5% in the assay.

In this assay, the compounds of the invention had $IC_{50}$ values provided infra:

| Example | SYK $IC_{50}$ [uM] |
|---|---|
| 1.1 | 0.023 |
| 1.2 | 0.0008 |
| 1.3 | 0.0035 |
| 1.4 | 0.001 |
| 2.1 | 0.012 |

-continued

| Example | SYK $IC_{50}$ [uM] |
|---|---|
| 2.2 | 0.0051 |
| 2.3 | 0.011 |
| 2.4 | 0.086 |
| 2.5 | 0.030 |
| 2.6 | 0.0046 |
| 3.1 | 0.0005 |
| 4.1 | 0.0027 |
| 4.2 | 0.001 |

[uM] means micromol per liter

Inhibition of the hERG (Human Ether-a-Gogo-Related-Gene) Channel (Manual Patch Clamp Assay)

The hERG patch clamp assay was done according to standard procedures used in Genetic Toxicology and Safety Pharmacology, based on recommendations and descriptions of methods in the literature, and according to current guidelines (ICH S7B, The non clinical evaluation of the potential for delayed ventricular repolarization (QT interval prolongation) by human pharmaceuticals, 2005). The purpose of the study is to assess the effect of the test item ABC123 on tail current recorded from HEK293 cells stably transfected with hERG cDNA. The HEK293 cells, which have been stably transfected with hERG cDNA, are a model considered to be suitable for this purpose (Zhou et al., 1998). Repolarisation of cardiac ventricular myocytes is mainly due to outward potassium currents. The most important current in humans is the delayed rectifier potassium current, $I_K$, which has both rapidly and slowly activating components ($I_{Kr}$ and $I_{Ks}$) (Sanguinetti and Jurkiewicz, 1990). The human ether-a-gogo-related-gene (hERG) encodes the major protein underlying $I_{Kr}$. Thus, inhibition of hERG potassium channels may lead to delayed cardiac repolarisation (Sanguinetti et al., 1995). Prolongation of cardiac repolarisation is a side effect that can be associated with some drug therapies. This proarrhythmic alteration is characterised by a prolongation of the QT interval in the surface electrocardiogram and is of particular concern because it may lead to the development of polymorphic ventricular arrhythmias like torsade de pointes (for review see: Vandenberg, Walker and Campbell, 2001). Compounds which inhibit the hERG current in vitro have been shown to possess the potential of prolonging the cardiac action potential and hence prolong the QT interval in man (Ficker et al., 1998; Kiehn et al., 1996; Mohammad et al., 1997).

HERG HEK (HEK293 cells stably transfected with hERG cDNA) obtained from the University of Wisconsin were used. For the experiments the cells were plated onto sterile Thermanox plastic coverslips (Nalge Nunc International) in 6-well plates. The dishes were stored in a humidified, gassed incubator. The coverslips with cells were transferred to the recording chamber and continuously superfused (at approximately 1-2 ml/min) with vehicle. The temperature of the vehicle in the bath chamber was regulated by temperature controllers to 35° C.±2.0° C. hERG currents were measured in the whole-cell patch-clamp configuration. Once a stable patch clamp configuration was achieved, recording commenced in voltage-clamp mode, with the cell initially clamped at −75 mV. hERG current was observed and recorded if a stable hERG tail current response could be induced. Afterwards the test item was perfused through the bath; fluid exchange took approximately 1-2 min to achieve the nominal test item concentration.

The hERG HEK293 cells were treated approximately 9 min with the test item. The following voltage protocol was applied to induce hERG currents: The step from −75 mV to +10 mV activates an outward current (i.e. current flows out of the cell) and the step from +10 mV to −40 mV produces the tail current (the tail current represents the time taken for the current to turn off). The voltage was held at +10 mV for 500 ms and at −40 mV for 500 ms, giving a total pulse length of 1 s. To determine the test item effect on the hERG current the voltage protocol was applied at a frequency of 0.1 Hz. The leak current was recorded and subtracted by a P/3n pulse between the voltage pulses (0.1 Hz).

REFERENCES RECITED IN THE ABOVE hERG-EXPERIMENT

ICH S7B: The non clinical evaluation of the potential for delayed ventricular repolarization (QT interval prolongation) by human pharmaceuticals, 2005.
[Ficker E, Jarolimek W, Kiehn J, et al. (1998)]. Molecular determinants of dofetilide block of HERG K+ channels. Circ Res; 82(3): 386-395.
[Kiehn J, Lacerda A E, Wible B, Brown A M (1996)]. Molecular physiology and pharmacology of HERG. Single-channel currents and block by dofetilide. Circulation; 94(10): 2572-2579.
[Mohammad S, Zhou Z, Gong Q, January C T (1997)]. Blockage of the HERG human cardiac K+ channel by the gastrointestinal prokinetic agent cisapride. Am J Physiol; 273(5 Pt 2): H2534-H2538.
[Sanguinetti M C, Jiang C, Curran M E, Keating M T (1995)]. A mechanistic link between an inherited and an acquired cardiac arrhythmia: HERG encodes the IKr potassium channel. Cell; 81(2): 299-307.
[Sanguinetti M C and Jurkiewicz N K (1990)]. Two components of cardiac delayed rectifier K+ current. Differential sensitivity to block by class III antiarrhythmic agents. J Gen Physiol; 96(1): 195-215.
[Trudeau M, Warmke J W, Ganetzky B, Robertson G A (1995)]. HERG, a human inward rectifier In the voltage-gated potassium channel family. Science; 269: 92-95.
[Vandenberg J I, Walker B D, Campbell T J (2001)]. HERG K+ channels: friend and foe. Trends Pharmacol Sci; 22(5): 240-246.
[Zhou Z, Gong Q, Ye B, Fan Z, Makielski J C, Robertson G A, January C T (1998)]. Properties of HERG channels stably expressed in HEK 293 cells studied at physiological temperature. Biophys J; 74(1): 230-241.

In this assay, the compounds of the invention have %-inhibition values provided infra:

| %-Inhibition of hERG channel activity | |
|---|---|
| Ex. 1.1 | Ex. 1.3 |
| not tested at 3 uM | 24 ± 3% at 3 uM |
| −5 ± 4% at 10 uM | 37 ± 6% at 10 uM |
| 12 ± 6% at 30 uM | 74 ± 6% at 30 uM | uM means micromol per liter

In Vitro Cellular Assays:
B Cell Receptor:
Anti IgM-induced phosphorylation of BLNK (BLNK=B cell linker (SLP65=SH2 domain containing leukocyte protein of 65 kDa)) in Ramos B cells:
Ramos B cells in a volume of 25 µl were incubated with 25 µl of the compound solution at 2-fold the desired final concentration for 30 min. at 37° C. Then 50 µL anti IgM was added, mixed and incubated for 15 min. at 37° C. In each experiment 8-fold serial dilutions of compounds were tested. The stimulation was stopped by addition of 100 µL/well of PFA (para formaldehyde)/PBS (phosphate buffered saline) (final conc. 2% PFA) for fixation and incubated for 15 min. at 37° C., then centrifuged at 1300 rpm for 3 min and permeabilized by resuspending the cell pellet in 100 µL methanol 90% and further incubated for 30 min at 4° C. The cells were then washed and phosphoproteins were detected by flow cytometry using fluorescently labeled anti-BLNK (pY84) (BD Biosciences).

Compounds of the inventions had the following efficacy in this assay:

| Example No | Anti IgM induced phosphorylation of BLNK in Ramos B cells; IC50 in nM |
|---|---|
| 1.1 | 106 |
| 1.2 | 63 |
| 1.3 | 72 |
| 1.4 | 14 |
| 2.1 | 121 |
| 2.2 | 58 |
| 2.3 | 393 |
| 2.4 | 890 |
| 2.5 | 106 |
| 2.6 | 37 |
| 3.1 | 25 |
| 4.1 | 28 |
| 4.2 | 36 |

Fc Gamma Receptor Assays:
FcR Stimulation-Induced SLP-76 Phosphorylation in Human Whole Blood Monocytes
Heparin—anticoagulated human whole blood (90 µL/well) was mixed with serial dilutions of compounds to be tested (10 µL per well) for 30 min at 37° C. followed by stimulation with anti CD32 antibody clone 6C4 for 5 min at 37° C. After lysis of erythrocytes and washings, the cell pellet was permeabilized with ice-cold methanol 90%. The permeabilized cells were washed and stained with anti CD14 (eBioscience) to detect monocytes and anti P-SLP76 (pY128) (BD Biosciences) and quantified by flow cytometry.

Compounds of the inventions had the following efficacy in this assay:

| Example No. | Fc Recepor stimulation induced SLP-76 (SH2 domain containing leukocyte protein of 76 kDa) phosphorylation in human whole blood monocytes, IC50 in nM |
|---|---|
| 1.1 | 378 |
| 1.2 | 491 |
| 1.3 | 447 |
| 1.4 | 177 |
| 2.1 | 509 |
| 2.2 | 394 |
| 2.5 | 671 |
| 2.6 | 562 |
| 4.1 | 311 |
| 4.2 | 596 |

B-Cell Lymphoma Cell Proliferation:
Cell proliferation was determined using the WST-1 assay (Roche, Mannheim, Germany), which measures the metabolic activity of the cells. Briefly, $5 \times 10^5$ TMD-8, OCl-Ly3, and OCl-Ly10 cells/well and $10 \times 10^5$ HBL-1 cells/well were seeded in triplicate in 96-well plates and were incubated with various concentrations of compounds to be tested for 3 days.

The cell proliferation reagent WST-1 (10 μl/well) was added to the cells for 1-2 hours depending on the cell type which were cultured in 200 μl of medium. The absorbance was then measured with an enzyme-linked immunosorbent assay plate reader at a wavelength of 450 nm. The concentrations required to inhibit growth by 50% (GI50) was assessed.

The following efficacy was determined for example 1.1:

| | Example 1.1 | | | |
|---|---|---|---|---|
| | Cell lines | | | |
| | TMD-8 | OCI-Ly3 | OCI-Ly10 | HBL-1 |
| GI50 (nM) | 281 | No inhibition | 25 | 105 |
| Days of incubation | 4 | 4 | 3 | 4 |

Utility Section

The compounds of the invention are therefore useful in the prevention or treatment of disorders or diseases where for example SYK inhibition plays a role, e.g. diseases or disorders mediated by, B lymphocytes, myeloid cells, neutrophils, mast cells, platelets basophils and/or eosinophils e.g. acute or chronic rejection of organ or tissue allo- or xenografts, atherosclerosis, vascular occlusion due to vacular injury such as angioplasty, restenosis, hypertension, heart failure, chronic obstructive pulmonary disease, CNS disease such as Alzheimer disease or amyotrophic lateral sclerosis, cancer, infectious disease such as AIDS, septic shock or adult respiratory distress syndrome, ischemia/reperfusion injury e.g. myocardial infarction, stroke, gut ischemia, renal failure or hermorrhage shock, or traumatic shock, gout, urticaria such as acute or chronic idiopathic or allergic urticaria, autoimmune hemolytic anemia, nephropathies such as IgA nephropathy, Sjögren's syndrome, cryoglobulinemias such as mixed cryoglobulinemia type I, II or III, inflammatory bowel diseases such as Crohn's disease or ulcerative colitis atherosclerosis, and osteoporosis.

In another embodiment compounds of the invention may in particular be for use in the prevention and/or treatment of urticaria, such as acute or chronic idiopathic or allergic urticaria.

The agent of the invention are also useful in the treatment and/or prevention of acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes mellitus (type I and II) and the disorders associated therewith, vascular manifestations of autoimmune and inflammatory diseases (vasculitides), respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis, immune and/or idiopathic thrombocytopenia, allergies, wound healing, and Graft vs host disease.

In another embodiment compounds of the invention may in particular be for use in the prevention and/or treatment of acute or chronic inflammatory diseases or disorders or autoimmune diseases e.g. rheumatoid arthritis, osteoarthritis, systemic lupus erythematosus, Hashimoto's thyroidis, multiple sclerosis.

In another embodiment compounds of the invention may in particular be for use in the prevention and/or treatment of immune and/or idiopathic thrombocytopenia.

Compounds of the invention are also useful in the prevention or treatment of tumors, for example brain and other central nervous system tumors (eg. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites, tumors of blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type e.g. diffuse large B cell lymphomas, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia.

In another embodiment compounds of the invention may in particular be for use in the prevention and/or treatment of leukemia of specified cell type e.g. diffuse large B cell lymphoma.

Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is.

Dosage(s), Administration(s):

For the above uses the required dosage will of course vary depending on the mode of administration, the particular condition to be treated and the effect desired. In general, satisfactory results are indicated to be obtained systemically at daily dosages of from about 0.02 to 25 mg/kg per body weight. An indicated daily dosage in the larger mammal, e.g. humans, may be typically in the range from about 0.2 mg to about 2 g, conveniently administered, for example, in divided doses up to four times a day or in retard form. Suitable unit dosage forms for oral administration may typically comprise from ca. 0.1 to 500 mg active ingredient.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration may for example be to the skin. A further form of topical administration may be to the eye. Pharmaceutical compositions comprising a compound of the invention in association with at least one pharmaceutical acceptable carrier or diluent may be manufactured in conventional manner by mixing with a pharmaceutically acceptable carrier or diluent.

The compounds of the invention may be administered in free form or in pharmaceutically acceptable salt form, e.g. as indicated above. Such salts may be prepared in conventional manner and may typically exhibit the same order of activity as the free compounds.

Combinations:

Compounds of the invention may be administered as the sole active ingredient or together with other drugs useful against neoplastic diseases, inflammatory disorders or in immunomodulating regimens. For example, the compounds of the invention may be used in combination with an active agent effective in various diseases as described above, e.g. with cyclosporins, rapamycins or ascomycins, or their immunosuppressive analogs or derivatives, e.g. cyclosporin A, cyclosporin G, Isa tx247, FK-506, sirolimus or everolimus; CCI-779, ABT578, AP23573, corticosteroids e.g. prednisone; cyclophosphamide; azathioprine; methotrexate; gold salts, sulfasalazine, antimalarials; leflunomide; mizoribine; mycophenolic acid; mycophenolate mofetil; 15-deoxyspergualine; an S1P receptor modulator having accelerating lymphocyte homing activity, e.g FTY720 or an analogue thereof, immuno-suppressive monoclonal antibodies, e.g. monoclonal antibodies to leukocyte receptors, e.g. MHC, CD2, CD3, CD4, CD7, CD25, CD28, CD40, CD45, CD58, CD80, CD86, CD152, CD137, CD154, ICOS, LFA-1, VLA-4 or their ligands; or other immunomodulatory compounds, e.g. CTLA4Ig;

Jak inhibitors, anti IL-17, IL-1, anti TNF, TNF receptor blocker, anti CD20, anti CD19, PI3 kinase inhibitors, or Btk inhibitors.

A compound of the invention may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. A combination of the invention comprising an antineoplastic agent which is an aromatase inhibitor may particularly be useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride.

The term "topoisomerase I inhibitors" as used herein includes, but is not limited to topotecan, irinotecan, 9-nitro-camptothecin and the macromolecular camptothecin conjugate PNU-166148 (compound A1 in WO99/17804).

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D.

The term "alkylating agents" as used herein includes, but is not limited to cyclophosphamide, ifosfamide and melphalan.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs), and anti-angiogenic compounds having another mechanism of action than decreasing the protein kinase activity.

The term "gonadorelin agonist" as used herein includes, but is not limited to abarelix, goserelin and goserelin acetate. Goserelin is disclosed in U.S. Pat. No. 4,100,274.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having aniproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

What is claimed is:

1. A compound according to formula (II) or a pharmaceutically acceptable salt thereof, wherein

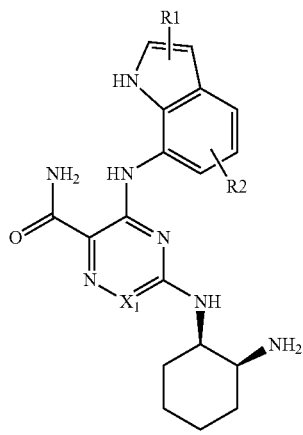

(II)

X1 is N;
R1 is H, $C_{1-4}$alkyl, CN, or Hal; and
R2 is H, $C_{1-4}$alkyl or Hal.

2. A compound of claim 1 or a pharmaceutically acceptable salt thereof, wherein
X1 is N;
R1 is H or methyl; and
R2 is H or fluoro.

3. A compound of claim 1 or a pharmaceutically acceptable salt thereof, wherein X1 is N, and wherein R1 and R2 are both hydrogen.

4. A compound in accordance to claim 1 or a pharmaceutically acceptable salt thereof, wherein said compound is selected from:
   3-((1R,2S)-2-Amino-cyclohexylamino)-5-(1H-indol-7-ylamino)-[1,2,4]triazine-6-carboxylic acid amide;
   3-((1R,2S)-2-Amino-cyclohexylamino)-5-(5-fluoro-3-methyl-1H-indol-7-ylamino)-[1,2,4]triazine-6-carboxylic acid amide;
   3-((1R,2S)-2-Amino-cyclohexylamino)-5-(3-methyl-1H-indol-7-ylamino)-[1,2,4]triazine-6-carboxylic acid amide;
   3-((1R,2S)-2-Amino-cyclohexylamino)-5-(3-chloro-1H-indol-7-ylamino)-[1,2,4]triazine-6-carboxylic acid amide;
   3-((1R,2S)-2-Amino-cyclohexylamino)-5-(3-cyano-1H-indol-7-ylamino)-[1,2,4]triazine-6-carboxylic acid amide; and
   3-((1R,2S)-2-Amino-cyclohexylamino)-5-(5-fluoro-1H-indol-7-ylamino)-[1,2,4]triazine-6-carboxylic acid amide.

5. A pharmaceutical composition comprising a therapeutically effective amount of a compound according to claim 1 and one or more pharmaceutically acceptable carriers.

6. A combination comprising a therapeutically effective amount of a compound according to claim 1 and one or more therapeutically active co-agents.

* * * * *